(12) United States Patent
Koseoglu

(10) Patent No.: US 11,155,757 B2
(45) Date of Patent: Oct. 26, 2021

(54) ISOMERIZATION PROCESS USING FEEDSTOCK CONTAINING DISSOLVED HYDROGEN

(71) Applicant: Saudi Arabian Oil Company, Dhahran (SA)

(72) Inventor: Omer Refa Koseoglu, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

(21) Appl. No.: 16/303,363

(22) PCT Filed: Jan. 18, 2018

(86) PCT No.: PCT/US2018/014195
§ 371 (c)(1),
(2) Date: Nov. 20, 2018

(87) PCT Pub. No.: WO2018/140279
PCT Pub. Date: Aug. 2, 2018

(65) Prior Publication Data
US 2020/0299593 A1    Sep. 24, 2020

Related U.S. Application Data

(63) Continuation-in-part of application No. 15/417,897, filed on Jan. 27, 2017, now abandoned.

(51) Int. Cl.
*C10G 45/58*    (2006.01)
*C10G 65/04*    (2006.01)
*C07C 5/27*     (2006.01)

(52) U.S. Cl.
CPC ............ *C10G 45/58* (2013.01); *C07C 5/2791* (2013.01); *C10G 65/043* (2013.01);
(Continued)

(58) Field of Classification Search
CPC ...... C10G 35/04; C10G 35/095; C10G 45/58; C10G 59/02; C10G 65/043; C07C 5/27; C07C 5/2724; C07C 5/2791
See application file for complete search history.

(56) References Cited

U.S. PATENT DOCUMENTS 4,804,803 A    2/1989  Schmidt et al.
4,923,589 A    5/1990  Dalson
(Continued)

FOREIGN PATENT DOCUMENTS

GB           906326 A       9/1962

OTHER PUBLICATIONS

International Search Report and Written Opinion, PCT/US2018/014195, dated May 4, 2018, 12 pages.

*Primary Examiner* — Renee Robinson
(74) *Attorney, Agent, or Firm* — Abelman, Frayne & Schwab

(57) ABSTRACT

A process and system is provided including hydroisomerization reaction zone for production of high octane gasoline blending components that provide high selectivity for producing high octane isomers of light paraffins. A light paraffin feed is enriched by incorporation of dissolved hydrogen, thereby permitting a reaction phase that is liquid or substantially liquid to produce high octane gasoline blending components. Accordingly, a substantially two phase isomerization reactor system is provided, with a hydrogen-enriched liquid feedstock phase and a solid phase catalyst.

29 Claims, 5 Drawing Sheets

(52) U.S. Cl.
 CPC .... *C07C 2523/42* (2013.01); *C07C 2527/126* (2013.01); *C10G 2300/1044* (2013.01); *C10G 2300/1081* (2013.01); *C10G 2300/202* (2013.01); *C10G 2300/305* (2013.01); *C10G 2300/4006* (2013.01); *C10G 2300/4012* (2013.01); *C10G 2300/4018* (2013.01); *C10G 2300/42* (2013.01)

(56) References Cited

U.S. PATENT DOCUMENTS

| | | |
|---|---|---|
| 5,294,328 A | 3/1994 | Schmidt et al. |
| 5,360,534 A | 11/1994 | Rice et al. |
| 5,382,730 A | 1/1995 | Breckenridge et al. |
| 6,177,601 B1 | 1/2001 | Bogdan et al. |
| 6,320,089 B1 * | 11/2001 | Gillespie ................ B01J 27/08 585/734 |
| 6,338,791 B1 | 1/2002 | Ragil et al. |
| 6,395,945 B1 | 5/2002 | Randolph |
| 7,514,590 B1 | 4/2009 | Rice |
| 7,638,674 B2 | 12/2009 | Rice et al. |
| 7,638,676 B2 | 12/2009 | Rice |
| 8,198,501 B2 | 6/2012 | Chen et al. |
| 2004/0247498 A1 | 12/2004 | Phillips et al. |
| 2005/0082202 A1 | 4/2005 | Ackerson et al. |
| 2013/0126392 A1 * | 5/2013 | Koseoglu ................ B01J 8/228 208/108 |
| 2013/0165713 A1 | 6/2013 | Chen et al. |
| 2014/0171706 A1 | 6/2014 | Glover |
| 2015/0175506 A1 | 6/2015 | Shakur |
| 2015/0191663 A1 | 7/2015 | Koseoglu |

\* cited by examiner

ISOMERIZATION PROCESS USING FEEDSTOCK CONTAINING DISSOLVED HYDROGEN

RELATED APPLICATIONS

This application is a United States national stage application under 35 USC § 371 of PCT/US2018/014195 filed Jan. 18, 2018, which claims the benefit of priority of U.S. patent application Ser. No. 15/417,897 filed Jan. 27, 2017, which is are both incorporated by reference herein.

BACKGROUND OF THE INVENTION

Field of the Invention

This invention relates to improved processes for the isomerization of light paraffins into branched isomers, and particularly to hydroisomerization processes using a hydrogen-enriched reactor feedstream.

Description of Related Art

Gasoline is generally prepared from a number of blend streams, including light naphtha, full range naphtha, heavier naphtha fractions, and heavy gasoline fractions. The gasoline pool typically includes butanes, light straight run, isomerate, FCC cracked products, hydrocracked naphtha, coker gasoline, alkylate, reformate, added ethers, etc. Of these, gasoline blend stocks from the FCC, the reformer and the alkylation unit account for a major portion of the gasoline pool.

For a given carbon number of a light naphtha component, the shortest, most branched isomer tends to have the highest octane number. For example, the single and double branched isomers of hexanes, mono-methylpentanes (i.e., Research Octane Number (RON) in the range of 74-76) and dimethylbutanes (i.e., RON in the range of 94-105) respectively, have octane numbers that are significantly higher than that of n-hexane (i.e., RON of about 25). Likewise, the single branched isomer of pentane, 2-methylbutane, has a significantly higher RON than n-pentane. By increasing the proportion of these high octane isomers in the gasoline pool, satisfactory octane numbers can be achieved for gasoline without additional additives.

Two types of octane numbers are currently being used, the motor octane number (MON) determined using ASTM D2700-11 ("Standard Test Method for Motor Octane Number of Spark-Ignition Engine Fuel") and the RON determined using ASTM D2699-11 ("Standard Test Method for Research Octane Number of Spark-Ignition Engine Fuel"). The two methods both employ the standard Cooperative Fuel Research (CFR) knock-test engine. Sometimes, the MON and RON are averaged, (MON+RON)/2, to obtain an octane number.

Gasoline suitable for use as fuel in an automobile engine should have a RON of at least 80, e.g., at least 85, or at least 90. High performance engines generally require a fuel having a RON of about 100. Most gasoline blending streams have a RON generally ranging from 55 to 95, with the majority typically falling between 80 and 90. It is desirable to maximize the amount of dimethylbutane in light paraffins of the gasoline pool to increase the overall RON.

Hydroisomerization is an important refining process whereby the RON of a refinery's gasoline pool can be increased by converting straight chain normal or singly branched $C_4$-$C_6$ light paraffins into more branched isomers. As an example of the octane impact of isomerization, consider the below equations:

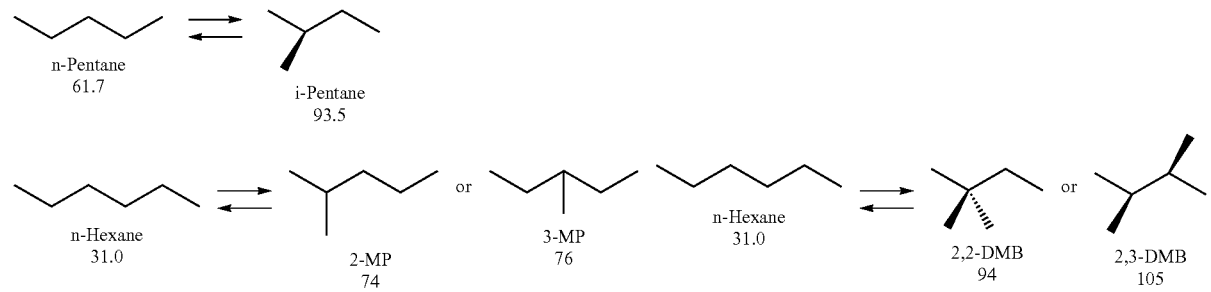

For n-pentane the increase will be by 32 points from 62 to 94; for n-hexane the increase will be by 43-74 points from 31 to 74-105, depending upon the isomer formed (2-MP: 2 methyl pentane, 3-MP: 3 methylpentane, 2,3-DMB: 2,3, dimethylbutane, 2,3-DMB: 2,3 dimethyl butane).

The process is typically carried-out a three-phase process, including hydrogen and light hydrocarbons, liquid gasoline, and solid catalyst. Conventional reactors operate at a pressure in the range of 15-40 bars and a temperature in the range of 120-280° C., although a person skilled in the art will appreciate that the design pressure is typically adjusted based on the feedstock composition.

The hydroisomerization reaction is controlled by thermodynamic equilibrium. At higher reaction temperatures, the equilibrium shifts towards the lower octane isomers (e.g., from dimethylbutanes via methylpentanes to n-hexane). Since the high octane components (e.g., 2,3-dimethylbutane with a RON of about 105) are the target products, improvements to conventional hydroisomerization in this field focus on development of active catalyst to perform this reaction at lower temperatures.

While improvements in the field can meet their intended purpose, a need remains for new and improved hydrocarbon hydroisomerization processes and systems.

SUMMARY OF THE INVENTION

In accordance with one or more embodiments, the invention relates to a system and process for isomerizing light paraffins into branched isomers, and particularly to hydroisomerization processes using a hydrogen-enriched reactor feedstream.

In accordance with one or more embodiments, a hydroisomerization reaction process and system is provided for production of high octane gasoline blending components that provide high selectivity for producing high octane isomers of light paraffins. A feedstock, such as a light paraffin feedstock, is enriched by incorporation of dissolved hydrogen, thereby permitting a reaction phase that is liquid or substantially liquid to produce high octane gasoline blending components. Accordingly, a substantially two phase isomerization reactor system is provided, with a hydrogen-enriched liquid feedstock phase and a solid phase catalyst.

BRIEF DESCRIPTION OF THE DRAWINGS

The invention will be described in further detail below and with reference to the attached drawings in which the same or similar elements are referred to by the same number, and where.

DETAILED DESCRIPTION OF THE INVENTION

Figure 1:
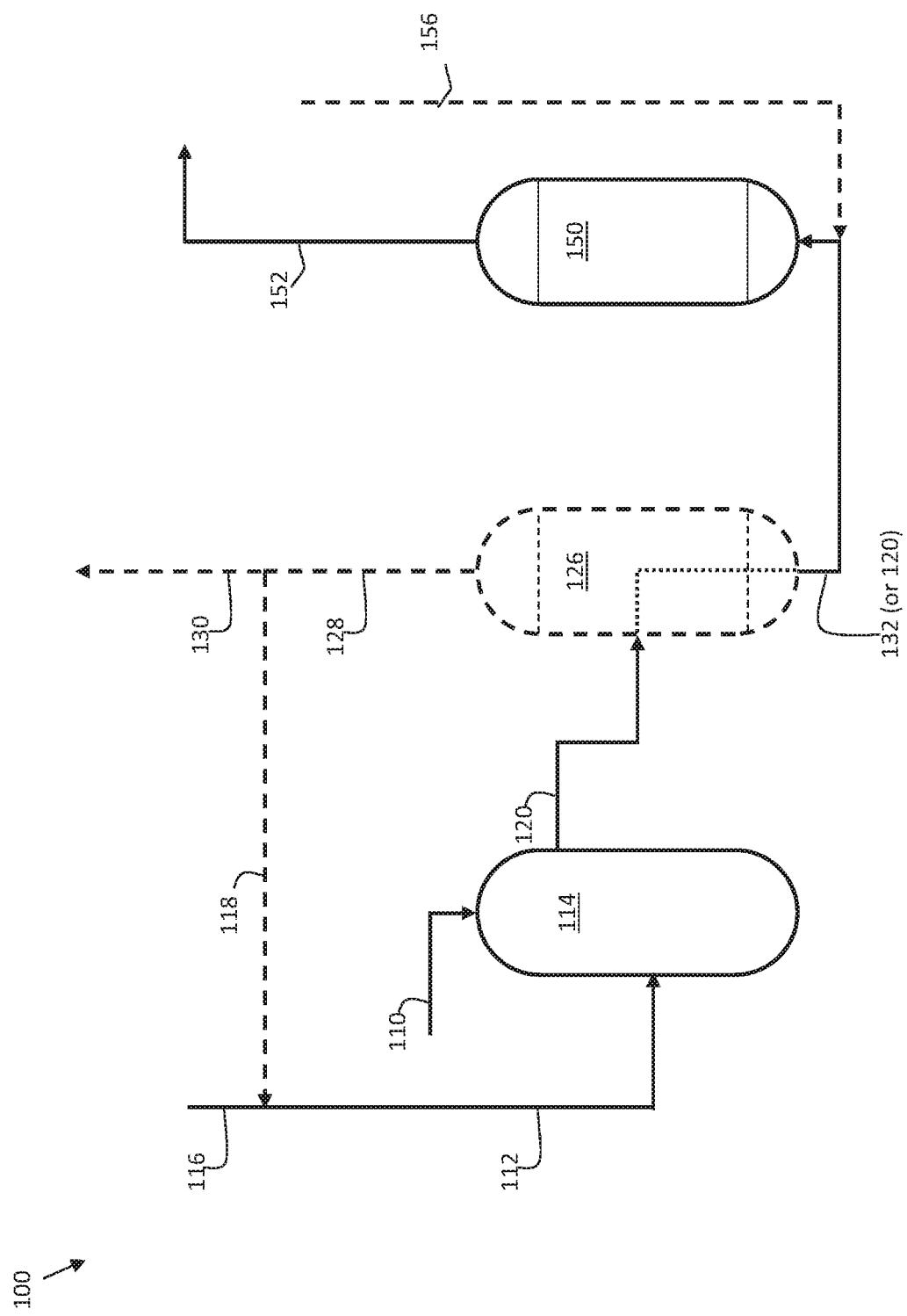
FIG. 1 is a process flow diagram of a system incorporating dissolved hydrogen in an isomerization process.

In the process and system described herein, hydroisomerization is carried out in the presence of solid catalyst to increase the quality of light hydrocarbon fractions and produce high octane gasoline blending components. The molecular structures of $C_4$-$C_8$ paraffinic hydrocarbons, in certain embodiments $C_4$-$C_6$, and in further embodiments $C_5$-$C_6$, are modified to increase the octane number. Hydroisomerization is conducted in a two-phase system, or a substantially two-phase system, where at least about 90 V % of the feedstock is maintained in liquid phase, in certain embodiments at least about 95 V %, and in further embodiments at least about 98 V %.

In the process and system herein, efficiency is improved and capital investment costs reduced by elimination or substantially reducing the requisite capacity of gas handling. The hydrogen gas phase is eliminated or substantially minimized by dissolving the hydrogen in liquid phase prior to passage in the reactor(s), resulting in a single phase or substantially single phase reactant mixture, referred to herein as a "hydrogen-enriched liquid feed," which is at least about 90 V % liquid phase, in certain embodiments at least about 95 V %, and in further embodiments at least about 98 V %. Accordingly, a two-phase or substantially two-phase hydroisomerization reaction zone is provided including the hydrogen-enriched liquid feed reactant mixture and the solid catalyst.

In the process, the feedstock and hydrogen gas are intimately mixed. The hydrogen-enriched liquid feed is sent to the isomerization reactor. In certain embodiments, if excess hydrogen is used, the combined stream of hydrogen-enriched feed and excess hydrogen is flashed and the hydrogen-enriched liquid feed is sent to the isomerization reactor. Using the system and process herein, the gas phase in the isomerization reactor is eliminated or minimized, and problems typically associated with gas hold-up in fixed-bed reactors of traditional design are minimized or eliminated.

The feedstock and hydrogen are mixed in a pipe or in a mixing vessel upstream of the hydroisomerization reaction zone. The feedstock having dissolved hydrogen therein, a liquid phase, is charged to an isomerization reactor containing an effective amount of solid isomerization catalyst materials. If necessary excess gas phase hydrogen is flashed, and the flash bottoms containing feedstock having dissolved hydrogen therein, a liquid phase, is charged to the isomerization reactor. Accordingly, a two-phase system, or a substantially two-phase system, is provided in the isomerization reactor.

A system and apparatus includes an isomerization reaction zone, and one or more upstream zones to dissolve an effective quantity of hydrogen gas in the paraffinic feedstock in a quantity effective to support isomerization reactions and provide a liquid phase or substantially liquid phase reactant mixture.

In certain embodiments these upstream zones effective to dissolve hydrogen gas in the paraffinic feedstock include: a mixing zone having hydrogen and feed inlets, and a mixture outlet for discharging reactants substantially in liquid phase. The mixture outlet is in fluid communication with one or more feed inlets of the isomerization reaction zone. In additional embodiments, the zones upstream of the isomerization reaction zone that are effective to dissolve hydrogen gas in the paraffinic feedstock include one or more conduits with integrated mixing apparatus, such as in-line mixers.

In certain embodiments these upstream zones effective to dissolve hydrogen gas in the paraffinic feedstock include: a mixing zone having hydrogen and feed inlets, and a mixture outlet; and a flashing zone having an inlet in fluid communication with the mixture outlet, a gas outlet, and an enriched-feed outlet for discharging reactants substantially in liquid phase. The enriched feed outlet is in fluid communication with one or more feed inlets of the isomerization reaction zone. Undissolved hydrogen and any light components are recovered from the gas outlet of the flash zone. In additional embodiments, the zones upstream of the isomerization reaction zone that are effective to dissolve hydrogen gas in the paraffinic feedstock include one or more conduits with integrated mixing apparatus, such as in-line mixers. In additional embodiments, the zones upstream of the isomerization reaction zone that are effective to dissolve hydrogen gas in the paraffinic feedstock include a flashing zone having an inlet in fluid communication with a conduit having an integrating mixing apparatus, a gas outlet, and an enriched-feed outlet for discharging reactants substantially in liquid phase.

In certain embodiments, a process for isomerization of a hydrocarbon feedstock into isomers of high octane number comprises:
  mixing feedstock in a mixing zone to dissolve a portion of the hydrogen gas in the liquid hydrocarbon feedstock to produce a hydrogen-enriched liquid hydrocarbon feedstock;
  passing the hydrogen-enriched liquid hydrocarbon feedstock from the mixing zone to the inlet of the isomerization reactor for reaction including isomerization of the feedstock into isomerates.

In further embodiments, a process for isomerization of a hydrocarbon feedstock into isomers of high octane number comprises:
  mixing feedstock and an excess of hydrogen gas in a mixing zone to dissolve a portion of the hydrogen gas in the liquid hydrocarbon feedstock to produce a hydrogen-enriched liquid hydrocarbon feedstock;

conveying the hydrogen-enriched liquid hydrocarbon feedstock and excess hydrogen to a flashing zone in which at least a portion of undissolved hydrogen gas is flashed; and passing the hydrogen-enriched liquid hydrocarbon feedstock from the flashing zone to the inlet of the isomerization reactor for reaction including isomerization of the feedstock into isomerates.

In certain embodiments, the process further includes separating the unconverted paraffins in separation step and recycling the unconverted paraffinic fed for mixing with fresh feedstock for reprocessing.

The feed for the process containing normal and single branched $C_5$-$C_8$ paraffins, in certain embodiments $C_5$-$C_6$, and in further embodiments $C_5$-$C_6$. The $C_5$-$C_8$ paraffins, in certain embodiments $C_5$-$C_6$, and in further embodiments $C_5$-$C_6$ components form a significant portion of the feed. Typically, such feeds have a RON of less than 60. Any suitable paraffin-containing feedstock may be used in the processes herein, including naphtha feedstocks including straight-run naphtha, natural gasoline, synthetic naphtha, thermal gasoline, catalytically cracked gasoline, partially reformed naphtha or raffinates from extraction of aromatics. Naphtha feedstocks comprise paraffins, naphthenes, and aromatics, and may comprise small amounts of olefins, boiling within the gasoline range. In certain embodiments the feedstock is a light naphtha mixture having an initial boiling point in the range of about 10° C. to about 65° C. and a final boiling point in the range of about 75° C. to about 110° C.

The isomerization reaction zone can include one or more fixed-bed, moving-bed, fluidized-bed or batch reactor systems. The reactants can be contacted with solid catalyst particles in an upward, downward, or radial-flow manner. The isomerization reaction zone can include a single reactor or multiple reactors with suitable fluid communication between reactors and thermal means and control to ensure that the desired isomerization temperature is maintained at the inlet to each zone.

Isomerization conditions in the isomerization reaction zone are maintained at levels effective to maintain at least about 90 V % of the feedstock in liquid phase, in certain embodiments at least about 95 V % in liquid phase, and in further embodiments at least about 98 V % in liquid phase. These conditions include reactor temperatures of from about 20° C. to 300° C., 20° C. to 285° C., 20° C. to 180° C., 50° C. to 300° C., 50° C. to 285° C., 50° C. to 180° C., 80° C. to 300° C., 80° C. to 285° C., 80° C. to 180° C., 100° C. to 300° C., 100° C. to 285° C., or 100° C. to 180° C. Lower reaction temperatures are generally preferred to favor equilibrium mixtures having the highest concentration of high-octane highly branched iso-alkanes and to minimize cracking of the feed to lighter hydrocarbons. In addition, the temperature range is also selected based on the type of catalyst. For instance, in embodiments in which Zirconia type catalysts are used, the temperature should be from about 200° C. to about 285° C. Reactor operating pressures generally range from about 10 to 100 bars, 10 to 70 bars, 20 to 100 bars, 20 to 70 bars, 30 to 100 bars, or 30 to 70 bars. In certain embodiments, for a pentane feedstock the reactor operating pressure is at least about 50 bars and for hexane and higher the reactor operating pressure is at least about 40 bars. Liquid hourly space velocities (LHSV) range from about 0.2 to 20 $h^{-1}$, 0.2 to 2 $h^{-1}$, 1 to 20 $h^{-1}$, or 1 to 2 $h^{-1}$.

Effective catalysts for use in one or more reactors in the isomerization include those known to persons having ordinary skill in the art. Isomerization catalysts include but are not limited to those that are amorphous, e.g. based upon amorphous alumina, or zeolitic, such as platinum on alumina, zeolite, chlorinated alumina, a sulfated zirconia and platinum, a platinum group metal on chlorided alumina, tungstated support of a Group IVB oxide or hydroxide, such as zirconium oxide or hydroxide. In certain embodiments the catalyst comprises 0.05 wt. % to 5 wt. % of the at least one Group VIIIB metal. In additional embodiments the catalyst comprises a base material including zeolite and metal oxides with metals from Group IIIA-B or IVA-B.

In preferred embodiments, the isomerization reaction zone under conditions effective to increase the RON for a typical feedstock, that is, having a RON of 60 or lower, to a RON of at least 80, in certain embodiments at least 85, and in further embodiments at least 90.

Figure 4:
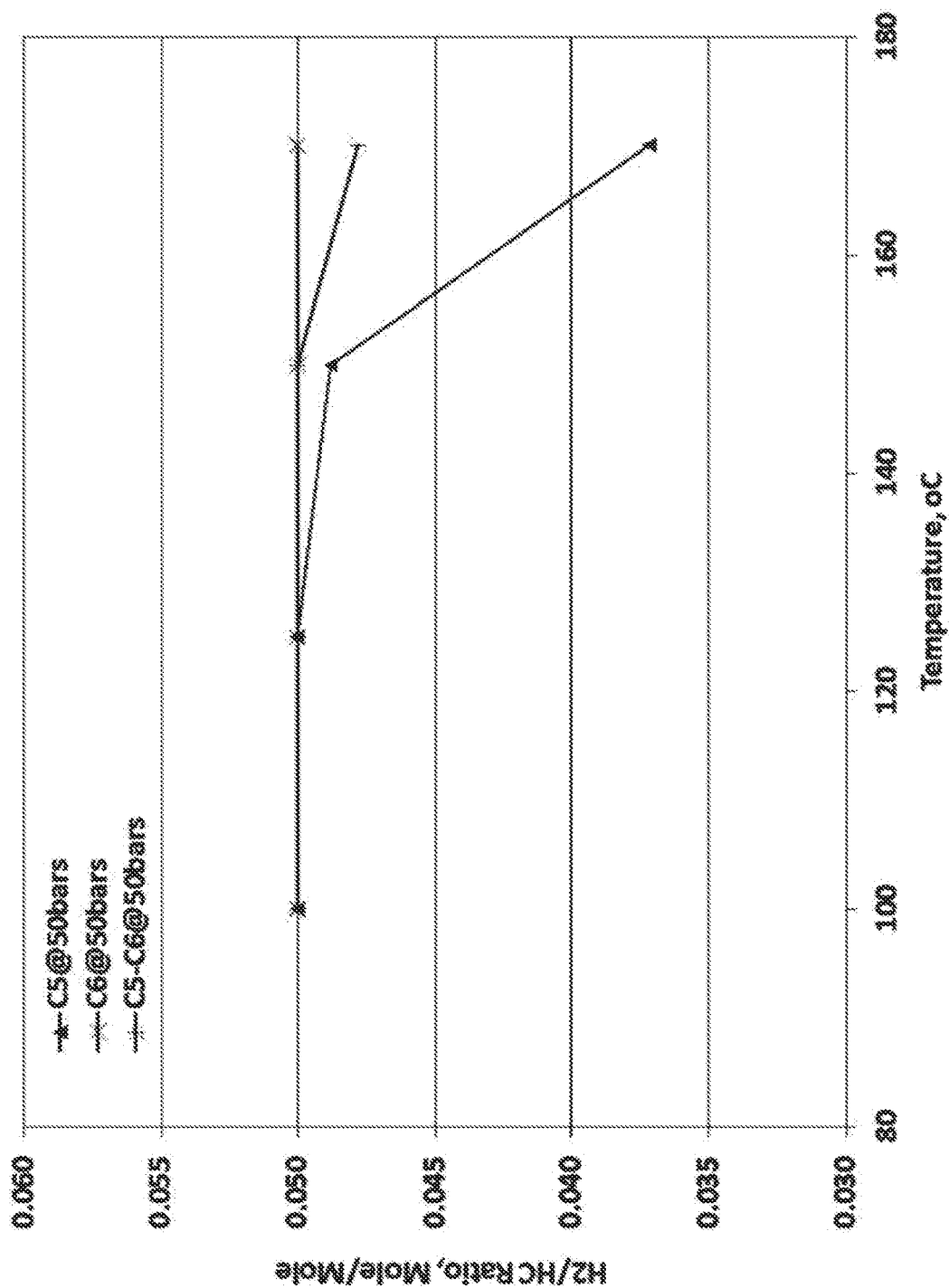
FIG. 4 is a plot of the ratio of hydrogen to hydrocarbon as a function of temperature and feed composition.

In the process herein, hydrogen is mixed with a paraffinic feedstock. The mixture of feedstock with hydrogen dissolved therein, hydrogen-enhanced feedstock, is sent to the isomerization reaction zone at a mole ratio of hydrogen to hydrocarbon feed of from about 0.01 to 20, 0.01 to 10, 0.01 to 1, 0.02 to 20, 0.02 to 10, 0.02 to 1, 0.05 to 20, 0.05 to 10, or 0.05 to 1. In the hydroisomerization reaction zone, relatively low hydrogen to feedstock ratios are effective, which minimize cracking reactions. For instance, FIG. 4 is a graphic plot (derived from PRO/II commercially available from Simulation Sciences Inc. of Brea, Calif.) of the hydrogen to hydrocarbon molar ratio as a function of for pentane, hexane and a mixture of 50:50 V % pentane and hexane at 50 bars at the reactor outlet.

For the purpose of this simplified schematic illustrations and description, the numerous valves, pumps, temperature sensors, electronic controllers and the like that are customarily employed in refinery operations and that are well known to those of ordinary skill in the art are not shown.

FIG. 1 is a process flow diagram of an isomerization process described herein that includes a hydrogen-enriched feedstock. In general, system 100 includes:

a mixing/distribution zone 114 (referred to herein as a mixing zone) having at least one inlet for receiving a light paraffin feed stream 110 and at least one inlet for receiving a hydrogen gas stream 112 (or alternatively a combined inlet for receiving both the feed and hydrogen gas), and an outlet for discharging a combined stream 120;

in certain embodiments, a flashing zone 126 (shown in dashed lines) having an inlet in fluid communication with the outlet discharging combined stream 120, a gas outlet 128 in fluid communication with one or more hydrogen gas inlets of the mixing zone 114, and an outlet for discharging hydrogen-enriched feedstock 132;

an isomerization reaction zone 150 having an inlet in fluid communication with the outlet for discharging a combined stream 120 shown in dotted lines overlaying the optional flashing zone 126) or outlet of flashing zone 126 for discharging hydrogen-enriched feedstock 132; and an isoparaffin-rich product outlet 152.

During operation of system 100, light paraffin feed stream 110 is intimately mixed with the hydrogen gas stream 112 in the mixing zone 114 to dissolve a predetermined quantity of hydrogen gas in the feed and produce a hydrogen-enriched light paraffin mixture. The hydrogen gas stream 112 includes fresh hydrogen introduced via stream 116 and optionally recycled hydrogen introduced via stream 118 (shown in dashed lines) from the optional flashing zone 126. In addition, in certain embodiments hydrogen can be recycled after separation from the reactor effluent (not shown). Light hydrocarbons and small amounts of inert material such as nitrogen and argon can be present in the hydrogen. Because of negligible cracking reactions, low hydrogen to feedstock ratios are used.

In certain embodiments, the combined stream 120 serves as the feed to the isomerization reaction zone 150. In embodiments in which excess hydrogen is used, stream 120 is conveyed to the flashing zone 126 in which the undissolved hydrogen and other gases (e.g., light feedstock fractions) are flashed off and removed as stream 128. The heavier fraction 132, which is the hydrogen-enriched hydrocarbon feedstock, serves as the feed to the isomerization reaction zone 150.

A portion 118 of stream 128 can optionally be recycled and mixed with the fresh hydrogen feed 116. The amount of recycled hydrogen in the hydrogen gas stream 112 generally depends upon a variety of factors relating to the excess undissolved hydrogen recovered from the flashing zone 126. For instance, the amount of stream 118 (relative to stream 128) can be in the range of about 50 to 100 V %, 50 to 99.5 V %, 50 to 99 V %, 50 to 95 V %, 80 to 100 V %, 80 to 99.5 V %, 80 to 99 V %, 80 to 95 V %, 90 to 100 V %, 90 to 99.5 V %, 90 to 99 V %, or 90 to 95 V %. A remaining portion of the flashed gases can be discharged from the system as a bleed stream 130, in embodiments where portion 118 is not 100 V % of stream 128. Bleed stream 130, the portion of stream 128 not recycled as stream 118, is effective to remove accumulated impurities. The hydrogen-enriched hydrocarbon feedstock stream 132 is introduced into the isomerization reaction zone 150, and an isomerate effluent stream containing branched paraffins is recovered from outlet 152. In certain embodiments, an additional feed 156 can also be introduced into the isomerization reaction zone 150.

The mixing zone 114 can be any apparatus that achieves the necessary intimate mixing of the liquid and gas so that sufficient hydrogen is dissolved in the liquid hydrocarbon feedstock. The mixing zone can include a combined inlet for the hydrogen and the feedstock or separate inlets as depicted. Mixing zone 114 can be a separate vessel or unit operation, in-line mixing apparatus, or a combination thereof to achieve the requisite hydrogen saturation.

Figure 2B:
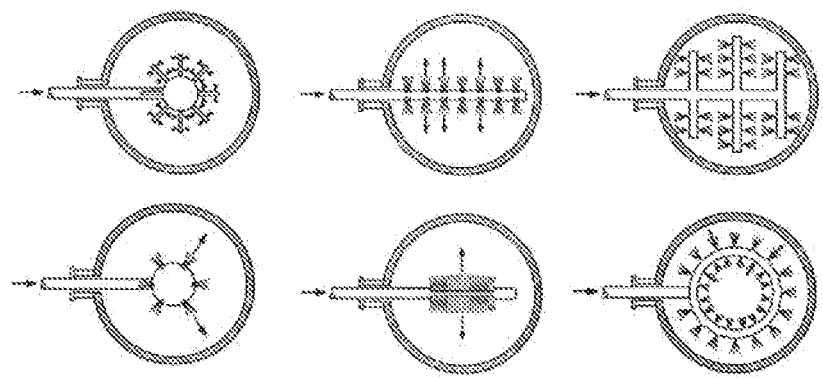
FIG. 2B shows gas distributors for use in a hydrogen dissolving system.

Effective unit operations include one or more gas-liquid distributor vessels, which apparatus can include spargers, injection nozzles, or other devices that impart sufficient velocity to inject the hydrogen gas into the liquid hydrocarbon with turbulent mixing and thereby promote hydrogen saturation. Suitable apparatus are described with respect to FIGS. 2A and 2B herein, and also, for instance, in U.S. Pat. Nos. 3,378,349; 3,598,541; 3,880,961; 4,960,571; 5,158,714; 5,484,578; 5,837,208; and 5,942,197, the relevant portions of which are incorporated herein by reference.

Figure 2A:
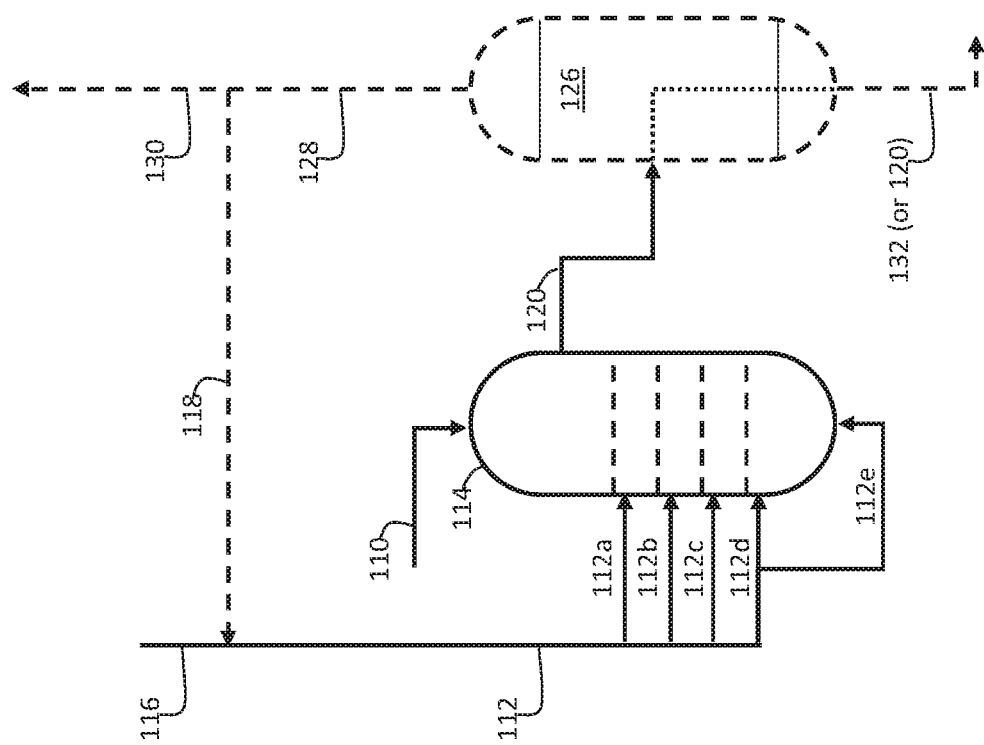
FIG. 2A a schematic diagram of a hydrogen dissolving system compatible with the method and apparatus of FIG. 1.

In certain embodiments, such as, for example, shown in FIG. 2A, a column is used as a hydrogen distributor vessel 114, in which hydrogen gas 112 is injected at plural locations 112a, 112b, 112c, 112d and 112e. Hydrogen gas is injected through hydrogen distributors into the column for adequate mixing to effectively dissolve hydrogen in the feedstock. For instance, suitable injection nozzles can be provided proximate several plates (locations 112a-112d) and also at the bottom of the column (location 112e). The liquid feedstock 110 can be fed from the top of the column as shown in the figure or from the bottom of the column (not shown).

Various types of hydrogen distributor apparatus can be used. For instance, referring to FIG. 2B, gas distributors can include tubular injectors fitted with nozzles and/or jets that are configured to uniformly distribute hydrogen gas into the flowing hydrocarbon feedstock in a column or vessel in order to achieve a saturation state in the mixing zone.

Operating conditions in the mixing zone 114 are selected to promote solubility of the hydrogen gas within the liquid hydrocarbon mixture. The mixing zone is maintained at pressure levels of from about 5 bars to about 200 bars, and at a ratio of the normalized volume of hydrogen to the volume of liquid hydrocarbon of about 30 to about 300 normalized liters of hydrogen per liter of liquid hydrocarbon.

The optional flashing zone 126 can include one or more flash drums that are maintained at suitable operating conditions to maintain an effective amount of hydrogen gas in solution in the light paraffin feed.

Figure 3:
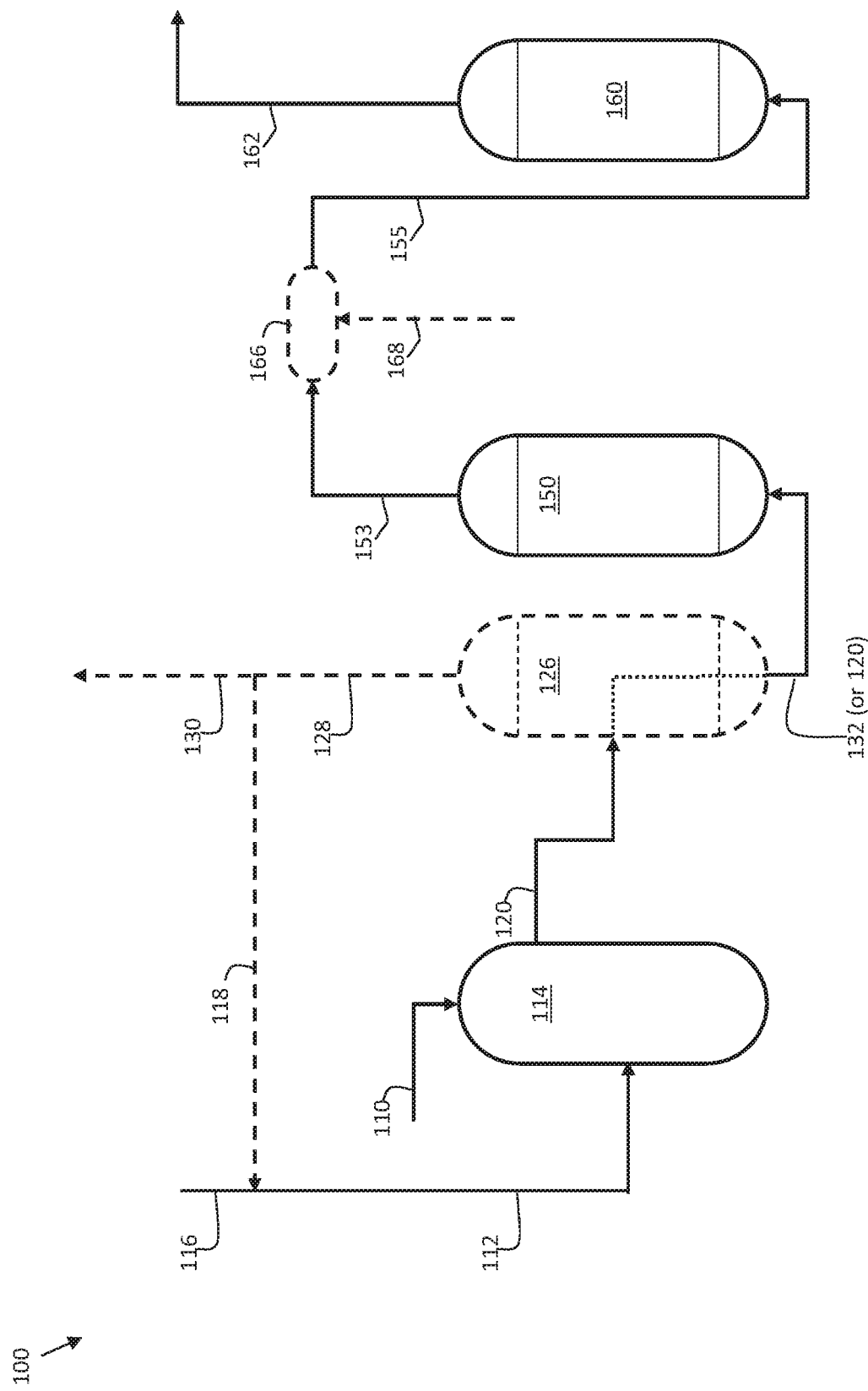
FIG. 3 is a process flow diagram of another embodiment of a system incorporating dissolved hydrogen in an isomerization process.

In embodiments in which multiple reactors are used in series, the intermediate feed to subsequent reactors is generally about 90 V % liquid phase, in certain embodiments at least about 95 V %, and in further embodiments at least about 98 V %. In certain embodiments multiple reactors in series are provided to control individual reactor operating conditions. Suitable fluid communication is provided between reactors and thermal means and control to ensure that the desired isomerization temperature is maintained at the inlet to each zone. FIG. 3 is a flow diagram of a process similar to that of FIG. 1 (including the mixing zone 114, the optional flashing zone 126 and the isomerization reaction zone 150 which are arranged and operate as described with respect to FIG. 1), in which effluent 153 from isomerization reaction zone 150 is an intermediate effluent that is passed to a second isomerization reaction zone 160. Further conversion to isomerates occurs in zone 160 and a product stream 162 is recovered. In processes in which there is pressure let-down or intermediate fractionation, an additional source of hydrogen 168 is provided (shown in dashed lines). In certain embodiments, this additional hydrogen can be mixed with an optional mixing zone 166 (shown in dashed lines) between the first and second isomerization reaction zones 150, 160 to provide a feed 155 to second isomerization reaction zone 160 that contains additional hydrogen. If the second isomerization reaction zone 160 operates as a two-phase system of the process herein, an additional optional flashing zone (not shown) can be provided between the mixing zone 166 and the second isomerization reaction zone 160, whereby the mixing zone 166 and the additional flashing zone operate as described herein with respect to the upstream mixing zone 114 and optional flashing zone 126.

Since the isomerization process proceeds toward a thermodynamic equilibrium, the isomerate will still contain normal paraffins that have low octane ratings. The presence of these normal paraffins in the isomerate is tolerable if there are sufficient quantity of other high quality gasoline blending components. In certain embodiment to produce higher RON isomerates, the isomerization processes can be modified with a separation step to isolate an iso-paraffin concentrate and a normal paraffin stream from the isomerate. The separated normal paraffin stream, for instance, in the range of about 30 W % to about 60 W %, can be recycled to initial feed (i.e., upstream of the mixing zone or in-line mixing apparatus in the present system and process) or to the isomerization reactor.

In certain embodiments, a separation section is provided in fluid communication with the outlet of the isomerization reaction zone, for instance, including one or more fractional distillation columns for separating lighter components from an isoparaffin-rich product from the isomerization reaction zone.

In certain embodiments, a molecular sieve adsorption process is used to separate normal paraffins from isoparaffins. This separation method relies on the pore size of the molecular sieve to selectively adsorb normal paraffins, due to the relatively smaller molecular diameter of normal paraffins compared to isoparaffins. As is known to those having ordinary skill in the art, the adsorption step is followed by a desorption step for net recovery of normal paraffins. These steps are carried out cyclically or pseudo-continuously. In certain embodiments additional fluid streams are used for the desorption and delivery steps.

In additional embodiments, a separation section is provided in fluid communication with the outlet of the isomerization reaction zone, for instance, including one or more fractional distillation columns for separating straight chain paraffins from branched paraffins. In certain embodiments one or more separation sections are provided for separating singly branched paraffins from paraffins with two or more branches. For instance, straight chain C5 and/or C6 paraffins in the isomerate reaction mixture can be separated from branched C5 and/or C6 paraffins. In additional embodiments, straight chain paraffins and singly branched C6 paraffins in the isomerate reaction mixture can be separated from C6 paraffins having two or more branches. All or a portion of the separated straight chain paraffins, and optionally the separated singly branched paraffins, can be recycled to the isomerization reactor, for instance, in the range of about 30 W % to about 60 W %.

In further embodiments, with or without a separation section, all or a portion of the isomerization reaction products can be recycled to the reactor to provide additional liquid medium to dissolve hydrogen, for instance, in the range of about 30 W % to about 60 W %.

All or part of the isoparaffin-rich product and/or the isoparaffin concentrate can be blended with finished gasoline along with other gasoline components from refinery processing including, but not limited to, one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to promote gasoline stability and uniformity, avoid corrosion and weather problems, maintain clean engine operation, and improve engine performance and drivability.

Hydrogen solubility is a function of pressure and temperature. Therefore, the liquid phase or substantially liquid phase isomerization reaction zone operates at a pressure and temperature sufficient to maintain the requisite quantity of hydrogen in the system. In certain embodiments, one or more lighter streams such as recycle streams from an isomerate separation step can be mixed with the initial feed to increase solubility of hydrogen in the hydrocarbon mixture.

Figure 5:
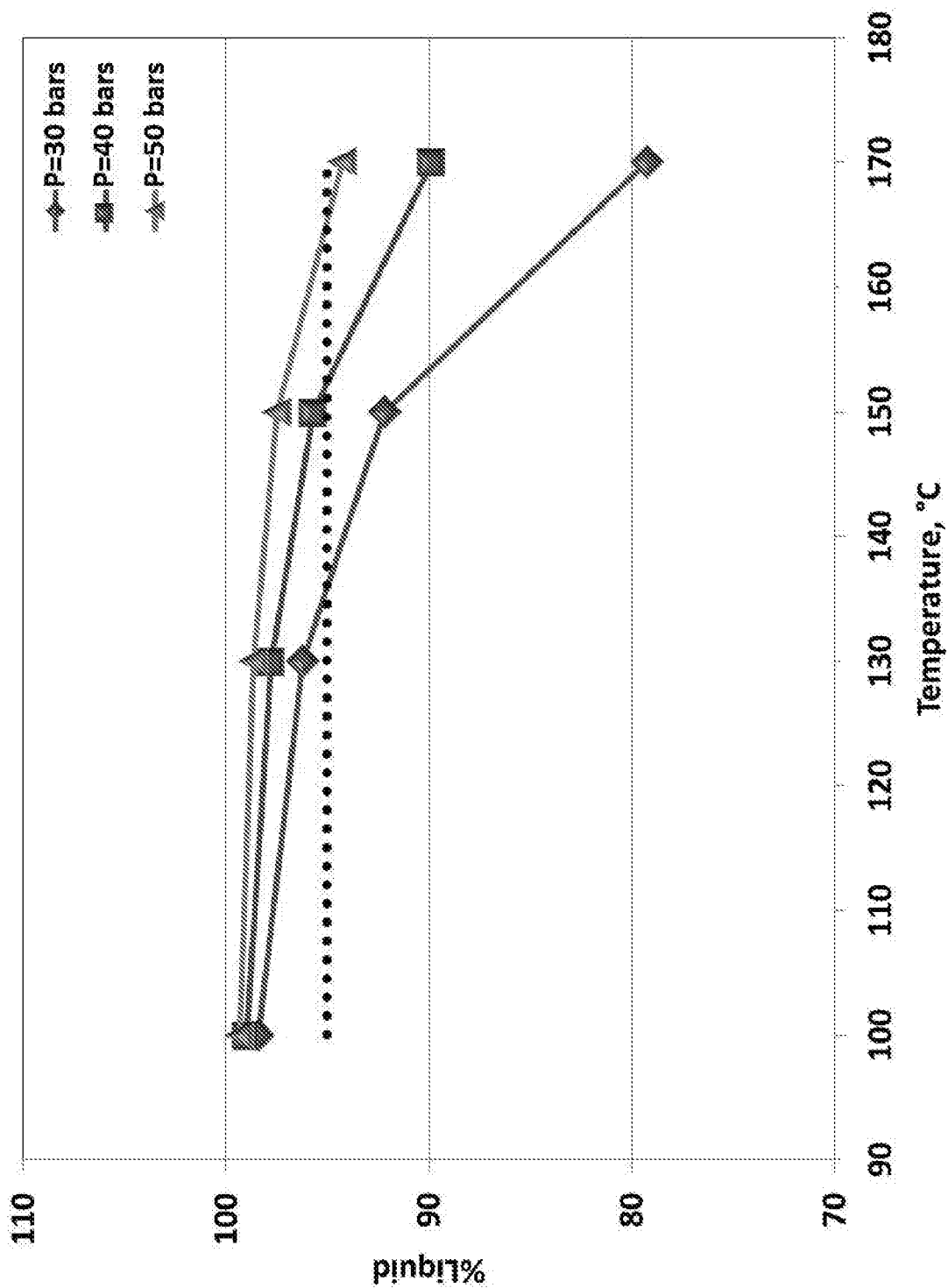
FIG. 5 is a plot of phase composition of light naphtha mixture as a function of temperature and pressure.

Using the mixing zone and flashing zone described herein, a functionally effective amount of hydrogen can be dissolved in the light paraffin feed. The amount of hydrogen dissolved in the feedstock depends on various factors, including the operating conditions of the mixing zone and the flashing zone, and the boiling point of the feed. FIG. 5 is a graphic plot (derived from PRO/II commercially available from Simulation Sciences Inc. of Brea, Calif.) of the liquid phase composition against system temperature for a mixture of 50:50 V % pentane and hexane at 30, 40 and 50 bars.

According to the process and system described herein, by using a hydrogen-enriched light paraffin feed which contains all or at least a substantial portion of the requisite hydrogen for hydroisomerization reactions as the feed through the isomerization reaction reactor(s), problems associated with excess gas in the system are alleviated. For example, since excess hydrogen gas in the system is minimized or substantially eliminated, the reactor effluent stream and the bottom stream have a reduced gas phase compared to conventional hydroisomerization systems, which will increase the efficiency and minimize the size and/or complexity of downstream separation equipment. The reduced levels of excess hydrogen also minimize the likelihood of gas hold-up, and the reactor volume can be used more effectively. A further advantage is that the reactor design can be simplified and therefore made more cost effective by eliminating or significantly reducing the gas phase.

EXAMPLE

The following example is derived using a commercial isomerization unit. Light straight run naphtha composed of n-pentane and n-hexane at 50:50 weight ratio with contaminants of less than 0.5 ppmw of sulfur and less 0.1 ppmw of nitrogen was used as a feed. Hydrogen was dissolved in the feed at a hydrogen to feedstock mole ratio of 0.05, and the isomerization reactions occurred in the presence of a platinum on chlorinated alumina catalyst at a temperature of 100° C., pressure of 50 bars, and LHSV of 1.6 $h^{-1}$ (calculated using PRO II, commercially available from Invensys System Inc. The isomerization reactor yielded an isomerate product having octane number of 81.4.

The method and system of the present invention have been described above and in the attached drawings; however, modifications will be apparent to those of ordinary skill in the art and the scope of protection for the invention is to be defined by the claims that follow.

The invention claimed is:

1. A process for isomerization of a gasoline pool feedstock comprising normal and single branched $C_4$-$C_6$ paraffins, the process comprising:

mixing the normal and single branched $C_4$-$C_6$ paraffinic feedstock, and hydrogen gas, in a mixing zone that comprises one or more gas-liquid distributor vessels that include a plurality of hydrogen distribution apparatus, each hydrogen distribution apparatus comprising a tubular injector fitted with a nozzle and/or a jet and that is configured to uniformly distribute hydrogen gas into the feedstock to achieve a saturation state in the mixing zone, to produce a mixture of hydrogen-enriched feedstock reactants;

contacting the hydrogen-enriched feedstock reactants with a solid isomerization catalyst for hydroisomerization in a substantially two-phase liquid-solid isomerization fixed-bed reaction zone under conditions that minimize cracking reactions and that are effective to isomerize paraffins in the gasoline pool feedstock into branched paraffins; and recovering an isomerate effluent stream.

2. The process of claim 1, wherein an excess of hydrogen gas is used, wherein the mixture comprises hydrogen-enriched feedstock reactants and undissolved hydrogen gas, the process further comprising separating the mixture of hydrogen-enriched feedstock and undissolved hydrogen into undissolved hydrogen and hydrogen-enriched feedstock reactants.

3. The process of claim 1, wherein the feedstock has a RON of 60 or less.

4. The process of claim 3, wherein the isomerate effluent stream has a RON of at least 80.

5. The process of claim 1, wherein the hydroisomerization conditions include a temperature of from 20° C. to 300° C.

6. The process of claim 1, wherein the hydroisomerization conditions include a temperature of from 100° C. to 180° C.

7. The process of claim 1, wherein the hydroisomerization conditions include a pressure of from 10 bars to 100 bars.

8. The process of claim 1, wherein the hydroisomerization conditions include a pressure of from 20 bars to 70 bars.

9. The process of claim 1, wherein the hydroisomerization conditions include a LHSV of 0.2 to 20 $h^{-1}$.

10. The process of claim 1, wherein the hydroisomerization conditions include a LHSV of 1 to 2 $h^{-1}$.

11. The process of claim 1, wherein the hydroisomerization conditions comprise a hydrogen to hydrocarbon mole ratio of 0.01 to 20.0.

12. The process of claim 1, wherein the hydroisomerization conditions comprise a hydrogen to hydrocarbon mole ratio of 0.02 to 10.0.

13. The process of claim 1, wherein the hydroisomerization conditions comprise a hydrogen to hydrocarbon mole ratio of 0.05 to 1.0.

14. The process of claim 1, wherein the hydroisomerization conditions are effective to maintain least 90 V % of the feedstock in liquid phase.

15. The process of claim 1, wherein the hydroisomerization conditions are effective to maintain least 95 V % of the feedstock in liquid phase.

16. The process of claim 1, wherein the hydroisomerization conditions are effective to maintain least 98 V % of the feedstock in liquid phase.

17. The process of claim 1, wherein the catalyst comprises 0.05 wt. % to 5 wt. % of the at least one Group VIIIB metal.

18. The process of claim 1, wherein the catalyst comprises a base material including zeolite and metal oxides with metals from Group IIIA-B or IVA-B.

19. The process of claim 1, further comprising separating the isomerate effluent stream into straight chain paraffins and branched paraffins.

20. The process as in claim 19, further comprising recycling the separated straight chain paraffins to the substantially two-phase liquid-solid isomerization reaction zone.

21. The process of claim 1, further comprising separating the isomerate effluent stream into straight chain paraffins/singly branched paraffins, and branched paraffins.

22. The process as in claim 21, further comprising recycling the straight chain paraffins/singly branched paraffins to the substantially two-phase liquid-solid isomerization reaction zone.

23. The process of claim 1, further comprising
contacting the isomerate effluent stream with a solid isomerization catalyst in a second isomerization reaction zone under conditions that minimize cracking reactions and that are effective for further isomerization; and
recovering a second reaction zone isomerate effluent stream.

24. The process of claim 23, wherein the second isomerization reaction zone operates as a substantially liquid-solid two-phase system.

25. The process of claim 23, further comprising mixing the isomerate effluent stream with hydrogen gas prior to contacting in the second reaction zone.

26. The process of claim 25, wherein the second isomerization reaction zone operates as a substantially liquid-solid two-phase system.

27. The process of claim 26, further comprising separating a mixture of hydrogen-enriched isomerate effluent stream reactants and undissolved hydrogen gas into undissolved hydrogen and hydrogen-enriched isomerate effluent, wherein hydrogen-enriched isomerate effluent is contacted in the second isomerization reaction zone.

28. The process of claim 1, wherein the one or more gas-liquid distributor vessels is a column having a top, a bottom and plural plates, and wherein a hydrogen distribution apparatus is included at the bottom and at each of the plates.

29. The process of claim 1, wherein the hydroisomerization conditions are effective to maintain at least 98 V % of the feedstock in liquid phase and include a temperature of from 100° C. to 180° C., a pressure of from 20 bars to 70 bars, a liquid hourly space velocity of 0.2 to 20 h−1, and a hydrogen to hydrocarbon mole ratio of 0.02 to 10.0.

* * * * *